(12) United States Patent
Muraoka (10) Patent No.: US 11,311,265 B2
(45) Date of Patent: Apr. 26, 2022

(54) RADIOGRAPHIC IMAGING SYSTEM, IMAGING CONTROL APPARATUS AND RADIOGRAPHIC IMAGING METHOD

(71) Applicant: Konica Minolta, Inc., Tokyo (JP)

(72) Inventor: Taketoh Muraoka, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 17/023,909

(22) Filed: Sep. 17, 2020

(65) Prior Publication Data

US 2021/0085276 A1 Mar. 25, 2021

(30) Foreign Application Priority Data

Sep. 19, 2019 (JP) .............................. JP2019-170007

(51) Int. Cl.
*A61B 6/00* (2006.01)
(52) U.S. Cl.
CPC ................. *A61B 6/54* (2013.01); *A61B 6/465* (2013.01)
(58) Field of Classification Search
CPC ........... A61B 6/54; A61B 6/545; A61B 6/465; A61B 6/548; A61B 6/56; A61B 6/461; A61B 5/5211; A61B 6/4233; A61B 6/463; A61B 6/5241; A61B 6/037; A61B 6/542; A62B 6/563; G06T 7/00
See application file for complete search history.

(56) References Cited

U.S. PATENT DOCUMENTS

2014/0254758 A1* 9/2014 Saigusa .................. A61B 6/545
378/62

FOREIGN PATENT DOCUMENTS

| JP | 2008-136751 A | 6/2008 |
| JP | 2009-240656 A | 10/2009 |
| JP | 2012-200398 A | 10/2012 |
| JP | 2018-011871 A | 1/2018 |
| JP | 2018-082922 A | 5/2018 |
| WO | 2013/103048 A1 | 7/2013 |
| WO | 2018/186275 A1 | 10/2018 |

OTHER PUBLICATIONS

JPO, Office Action for the related Japanese Patent Application No. 2019-170007, dated Dec. 1, 2020, with English translation.

* cited by examiner

*Primary Examiner* — Don K Wong
(74) *Attorney, Agent, or Firm* — Lucas & Mercanti, LLP

(57) ABSTRACT

A radiographic imaging system includes a radiation emitter, an image generator and a hardware processor. The radiation emitter emits radiation. The image generator generates a dynamic image composed of a plurality of frames according to received radiation The hardware processor determines at a predetermined timing whether at least one imaging allowing condition is satisfied. In response to determining that the at least one imaging allowing condition is satisfied, the hardware processor allows at least one of the radiation emitter and the image generator to operate.

21 Claims, 3 Drawing Sheets

RADIOGRAPHIC IMAGING SYSTEM, IMAGING CONTROL APPARATUS AND RADIOGRAPHIC IMAGING METHOD

CROSS-REFERENCE TO RELATED APPLICATIONS

The entire disclosure of Japanese Patent Application No. 2019-170007 filed on Sep. 19, 2019 is incorporated herein by reference in its entirety.

BACKGROUND

Technological Field

The present disclosure relates to a radiographic imaging system, an imaging control apparatus and a radiographic imaging method.

Description of the Related Art

Preparations for imaging of a radiograph(s) (a still image or (frames of) a dynamic image) (hereinafter "radiographic imaging") are complicated. Hence, a photographer (radiographer or the like) who photographs a large number of examinees per day may neglect to check whether preparations for imaging have been appropriately performed, or may overlook some of the preparations. Further, even when preparations for imaging are routinized, the imaging method may differ depending on the physical condition or the state of an examinee. For these reasons, the photographer may overlook essential items to check, or neglect to check whether preparations for imaging have been appropriately performed. As a result, the photographer may start imaging in a state in which preparations for imaging have not finished.

Further, during imaging, some kind of improperness (body motion of an examinee, etc.) may occur.

If imaging is performed without noticing that preparations for imaging have not finished or that improperness occurs, it is determined after imaging that imaging has failed (re-imaging is necessary). Re-imaging excessively restrains and uselessly exposes the examinee to radiation by the time length and the radiation dose of one time of radiographic imaging, which leads to increase in strain on the examinee. In addition, necessity of re-imaging delays the subsequent works, which leads to decrease in work efficiency of the photographer and increase in waiting time of another examinee(s).

Various technologies have been proposed to prevent imaging from starting in a state in which preparations for imaging have not finished and to prevent imaging from continuing in a state in which improperness occurs.

For example, there is disclosed in JP 2008-136751 A a mobile X-ray apparatus that, after X-ray imaging, interlocks control of an X-ray emitting unit from when image data is read out from an imaging plate until when captured data is erased from the imaging plate.

Further, there is disclosed in JP 2009-240656 A an X-ray imaging apparatus that monitors presence/absence of body motion of an examinee while long-length imaging is being performed, and emits a warning when the body motion of the examinee is detected.

SUMMARY

Unlike imaging of a still image(s), in imaging of a dynamic image(s) composed of a plurality of frames (hereinafter "dynamic imaging"), emission of radiation and generation of a radiograph (frame) are performed multiple times in a short time. In dynamic imaging, it may be necessary to perform preparations peculiar to dynamic imaging or to deal with improperness peculiar to dynamic imaging.

However, the technologies disclosed in JP 2008-136751 A and JP 2009-240656 A are both for imaging of a still image(s). Hence, the abovementioned technologies may be unable to deal with, in dynamic imaging, a case where proper preparations for imaging have not been performed and a case where improperness occurs.

The present disclosure has been made in view of the abovementioned problems, and objects thereof include, in radiographic imaging, preventing imaging from starting without proper preparations and from continuing despite of occurrence of improperness.

In order to achieve at least one of the abovementioned objects, according to a first aspect of the present disclosure, there is provided a radiographic imaging system including:
- a radiation emitter that emits radiation;
- an image generator that generates a dynamic image composed of a plurality of frames according to received radiation; and
- a hardware processor that
  - determines at a predetermined timing whether at least one imaging allowing condition is satisfied, and
  - in response to determining that the at least one imaging allowing condition is satisfied, allows at least one of the radiation emitter and the image generator to operate.

In order to achieve at least one of the abovementioned objects, according to a second aspect of the present disclosure, there is provided an imaging control apparatus including a hardware processor that
- determines at a predetermined timing whether at least one imaging allowing condition is satisfied, and
- in response to determining that the at least one imaging allowing condition is satisfied, allows at least one of an radiation emitter that emits radiation and an image generator that generates a dynamic image composed of a plurality of frames according to received radiation to operate.

In order to achieve at least one of the abovementioned objects, according to a third aspect of the present disclosure, there is provided a radiographic imaging method including:
- determining at a predetermined timing whether at least one imaging allowing condition is satisfied, and
- in response to determining that the at least one imaging allowing condition is satisfied, allowing at least one of an radiation emitter that emits radiation and an image generator that generates a dynamic image composed of a plurality of frames according to received radiation to operate.

BRIEF DESCRIPTION OF THE DRAWINGS

The advantages and features provided by one or more embodiments of the present invention will become more fully understood from the detailed description given hereinbelow and the appended drawings that are given by way of illustration only, and thus are not intended as a definition of the limits of the present invention, wherein.

DETAILED DESCRIPTION OF EMBODIMENTS

Hereinafter, one or more embodiments of the present invention will be described in detail with reference to the drawings.

However, the scope of the present invention is not limited to the disclosed embodiments or illustrated examples.

[1. Radiographic Imaging System]

First, a schematic configuration of a radiographic imaging system 100 (hereinafter "system 100") according an embodiment(s) will be described.

Figure 1:
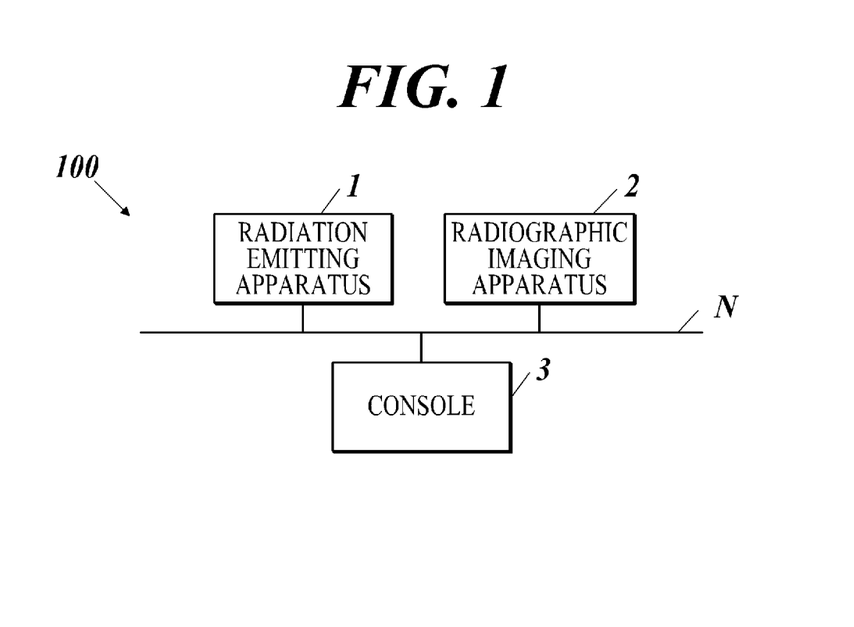
FIG. 1 is a block diagram showing a radiographic imaging system according to an embodiment(s) of the present disclosure.

FIG. 1 is a block diagram showing the system 100.

As shown in FIG. 1, the system 100 includes a radiation emitting apparatus (hereinafter "emitting apparatus 1"), a radiographic imaging apparatus (hereinafter "imaging apparatus 2") and a console 3.

These apparatuses are communicable with one another via a communication network N.

The system 100 may be connectable to other systems, such as a radiology information system (RIS) and a picture archiving and communication system (PACS) (not shown).

The system 100 may include an imaging table (for upright imaging, decubitus imaging, long-length imaging, etc.) (not shown) that holds the imaging apparatus 2.

The system 100 may further include a portable terminal (wearable terminal included) (not shown) having a display.

The system 100 may be fixed in an imaging room or may be configured as a nursing cart (the emitting apparatus 1 configured to be movable and the imaging apparatus 2 being portable).

(1-1. Radiation Emitting Apparatus)

The emitting apparatus 1 (radiation emitter) includes a generator, a vacuum tube (e.g. X-ray tube) and an operation device.

The generator applies, to the vacuum tube, a voltage suitable for preset imaging conditions (tube voltage, tube current, emission time (mAs value), etc.), on the basis of a control signal input from the operation device.

When receiving the voltage applied by the generator, the vacuum tube emits a dose of radiation (e.g. X-rays) corresponding to the applied voltage.

The operation device has an emission instructing switch (not shown) operable by a user (photographer, etc.), and outputs, to the generator, a control signal corresponding to an operation performed on the emission instructing switch.

The emitting apparatus 1 may be fixed in an imaging room or may be configured as a nursing cart to be movable together with the console 3 and/or the like.

The emitting apparatus 1 emits radiation in a mode suitable for the set imaging conditions by being triggered, for example, by an operation performed on the emission instructing switch.

For example, when an imaging mode that has been set is imaging of a still image (hereinafter "still image shooting"), the emitting apparatus 1 emits a predetermined dose of radiation for a predetermined emission time only once.

On the other hand, when the set imaging mode is imaging of a dynamic image (hereinafter "dynamic imaging"), the emitting apparatus 1 emits a predetermined dose of pulsed radiation for a predetermined emission time a predetermined number of times at predetermined intervals (on a predetermined cycle), wherein the emission time is shorter than the emission time for still image shooting.

In the case of dynamic imaging, the emitting apparatus 1 may keep emitting radiation while the emission instructing switch keeps being operated.

(1-2. Radiographic Imaging Apparatus)

The imaging apparatus 2 (image generator) includes a radiation detector, a scanning drive unit, a reader, an image generating unit and a communication unit (all not shown).

The radiation detector is configured such that pixels each having a radiation detection element and a switch element are arranged two-dimensionally (in a matrix). Each radiation detection element generates electric charges corresponding to a dose of received radiation.

The scanning drive unit controls ON/OFF of each switch element.

The reader reads out the amount of electric charges released from each pixel as a signal value.

The image generating unit generates image data of a radiograph(s) (a still image or (frames of) a dynamic image) from a plurality of signal values that have been read out.

The communication unit can send and receive data and signals to and from other apparatuses (emitting apparatus 1, console 3, etc.).

The imaging apparatus 2 may have a built-in scintillator, and convert received radiation into light having another wavelength, such as visible light, with the scintillator, and generate electric charges corresponding to the light obtained by the conversion, which is called indirect type, or may generate electric charges directly from received radiation without a scintillator or the like, which is called direct type.

The imaging apparatus 2 may be fixed in an imaging room or may be configured as a nursing cart to be movable together with the console 3 and/or the like.

The imaging apparatus 2 generates a radiograph(s) in a mode suitable for the set imaging conditions by being triggered, for example, by a predetermined control signal received from the console 3 or radiation received from the emitting apparatus 1.

For example, when the set imaging mode is still image shooting, the imaging apparatus 2 performs an imaging process (accumulates and releases electric charges, reads out signal values and generates image data) once.

On the other hand, when the set imaging mode is dynamic imaging, the imaging apparatus 2 repeats the imaging process a predetermined number of times on a predetermined cycle. That is, the imaging apparatus 2 generates a dynamic image composed of a plurality of frames according to received radiation In the case of dynamic imaging, the imaging apparatus 2 may generate a frame each time a timing signal that has been input is turned on, or may automatically repeat generation of a radiograph (frame) a predetermined number of times on a predetermined cycle, thereby generating a plurality of radiographs (frames), once the imaging apparatus 2 receives a signal that serves as a trigger for starting imaging (1-3. Console)

The console 3 as an imaging control apparatus is composed of a PC, a portable terminal or a dedicated apparatus.

The console 3 and the imaging control apparatus may be provided separately.

Hereinafter, the console 3 (imaging control apparatus) will be described in detail.

[2. Details of Imaging Control Apparatus]

Figure 2:
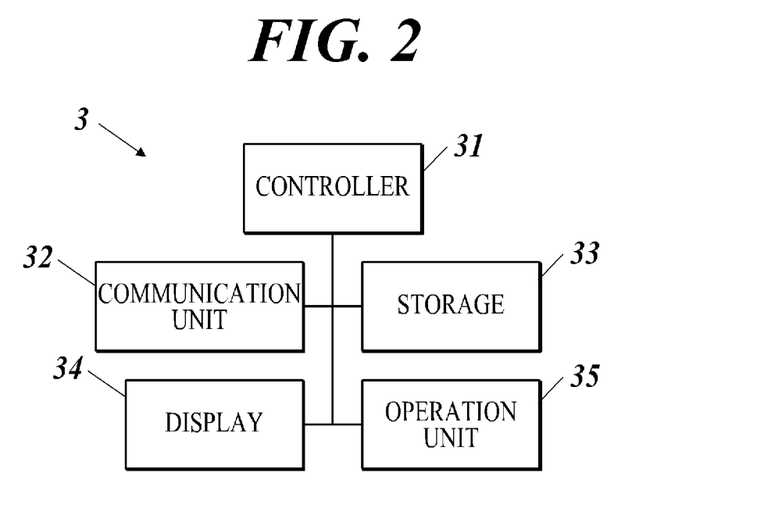
FIG. 2 is a block diagram showing an imaging control apparatus (console) of the radiographic imaging system shown in FIG. 1.

The console 3, which is the imaging control apparatus, of the system 100 will be described in detail. FIG. 2 is a block diagram showing the console 3.

(2-1. Configuration)

As shown in FIG. 2, the console 3 includes a controller 31 (hardware processor), a communication unit 32, a storage 33, a display 34 and an operation unit 35.

The controller 31 includes a CPU (Central Processing Unit) and a RAM (Random Access Memory). The CPU of the controller 31 reads out various programs stored in the storage 33, loads the programs into the RAM, and performs various processes in accordance with the loaded programs, thereby performing centralized control of operation of each component of the console 3.

The communication unit 32 includes a wired communication module or a wireless communication module, and can send and receive a variety of signals and a variety of data to and from other apparatuses (emitting apparatus 1, imaging apparatus 2, etc.) connected via the communication network N (LAN (Local Area Network), WAN (Wide Area Network), Internet, etc.) using cables or wirelessly.

The storage 33 is composed of a nonvolatile semiconductor memory, a hard disk and/or the like.

The storage 33 stores the programs that are executed by the controller 31 to perform various processes, parameters necessary for execution of the programs, and so forth.

The storage 33 also stores a plurality of candidates for imaging allowing conditions (imaging-allowing-condition candidates).

The storage 33 according to this embodiment stores a plurality of candidates A and a plurality of candidates B.

At least one (type) of the plurality of candidates A and the plurality of candidates B may be stored in a storage (e.g. a storage (not shown) of the emitting apparatus 1 or the imaging apparatus 2) different from the storage 33.

The candidates A are candidates for imaging allowing conditions the satisfaction or dissatisfaction of which is determined before the emitting apparatus 1 emits radiation The candidates A according to this embodiment include the following five candidates (a1) Explanation has been given to an examinee.
(a2) An audio guide has been tested.
(a3) Positioning of an examinee has been performed.
(a4) The emitting apparatus 1 and the imaging apparatus 2 are ready.
(a5) An examinee is equipped with an imaging aid(s).

Although the storage 33 according to this embodiment stores all of these five candidates, the candidates A exemplified herein are merely examples, and hence the number of candidates A and/or contents of candidates A can be changed according to operation of a facility where the system 100 is installed. That is, the storage 33 may store one or more of the above candidates a1 to a5, and/or may store one or more candidates different from the candidates a1 to a5.

Examples of the candidates that are different from the candidates a1 to a5 include: a condition that an examinee is a subject of an order received from an HIS or a RIS; a condition that, in radiographic imaging that needs an assist from a technician (e.g. photographer/radiographer) in an imaging room, the technician wears a radiation protective suit; and a condition that a pacemaker, an IV infusion set, a supporter, a jewelry and/or the like with which an examinee is equipped does not affect imaging.

The candidates B are candidates for imaging allowing conditions the satisfaction or dissatisfaction of which is determined while the emitting apparatus 1 is emitting radiation (a period during which the emitting apparatus 1 repeats emission of pulsed radiation included).

The candidates B according to this embodiment include the following four candidates.

(b1) An imaging target part of an examinee is in an irradiation field.
(b2) The dose of radiation is in a predetermined range.
(b3) An examinee has not moved more than a predetermined amount.
(b4) No request to stop has been made by an examinee.

Although the storage 33 according to this embodiment stores all of these four candidates, the candidates B exemplified herein are merely examples, and hence the number of candidates B and/or contents of candidates B can be changed according to operation of a facility where the system 100 is installed. That is, the storage 33 may store one or more of the above candidates b1 to b4, and/or may store one or more candidates different from the candidates b1 to b4.

Thus, the storage 33 according to this embodiment stores a plurality of candidates A and a plurality of candidates B.

How to use these candidates A and candidates B will be described later.

The display 34 is composed of a monitor, such as an LCD (Liquid Crystal Display) or a CRT (Cathode Ray Tube), and displays a variety of images, a variety of information and so forth in accordance with instructions of display signals input from the controller 31.

The operation unit 35 is composed of, for example: a keyboard including cursor keys, number input keys, various function keys and so forth; a pointing device, such as a mouse; and/or a touchscreen overlaid on the surface of the display 34, and is operable by a user.

The operation unit 35 outputs, to the controller 31, control signals based on operations performed thereon by the user.

(2-2. Operation)

The controller 31 of the console 3 thus configured can set the above imaging conditions in the emitting apparatus 1 and the imaging apparatus 2.

The console 3 can cause the display 34 to display the set imaging conditions.

Further, the console 3 can obtain radiographs generated by the imaging apparatus 2, and cause the display 34 to display the radiographs.

The controller 31 has a function of setting, as an imaging allowing condition(s), at least one candidate A and/or at least one candidate B selected based on a user's choice(s) from the candidates A and/or the candidates B for imaging allowing conditions stored in the storage 33.

In the case where another apparatus has a function of receiving user's choices, the controller 31 sets an imaging allowing condition(s) on the basis of a control signal(s) input from the apparatus.

The controller 31 according to this embodiment causes the display 34 to display, for example, a list of candidates for imaging allowing conditions, in order to receive user's choices of candidates.

When the user performs an operation on the operation unit 35 for choosing a candidate (e.g. presses a key corresponding to a candidate to choose, puts a cursor on a candidate to choose and clicks thereon, touches a display section of a candidate to choose, etc.), and consequently a candidate is selected (e.g. a checkmark is displayed in a checkbox, a candidate is displayed in a display section for a selected candidate(s), etc.), the controller 31 sets the selected candidate (A or B) as an imaging allowing condition (A or B) the satisfaction or dissatisfaction of which is determined at a predetermined timing.

The set imaging allowing condition(s) the satisfaction or dissatisfaction of which is determined before the emitting apparatus 1 emits radiation includes at least one (more than one, in this embodiment) of the candidates A (a1 to a5 and others).

The set imaging allowing condition(s) the satisfaction or dissatisfaction of which is determined while the emitting apparatus 1 is emitting radiation includes at least one of the candidates B (b1 to b4 and others).

In this embodiment, the controller 31 sets both imaging allowing conditions A and imaging allowing conditions B, but may set only an imaging allowing condition(s) A or only an imaging allowing condition(s) B.

Figure 3:
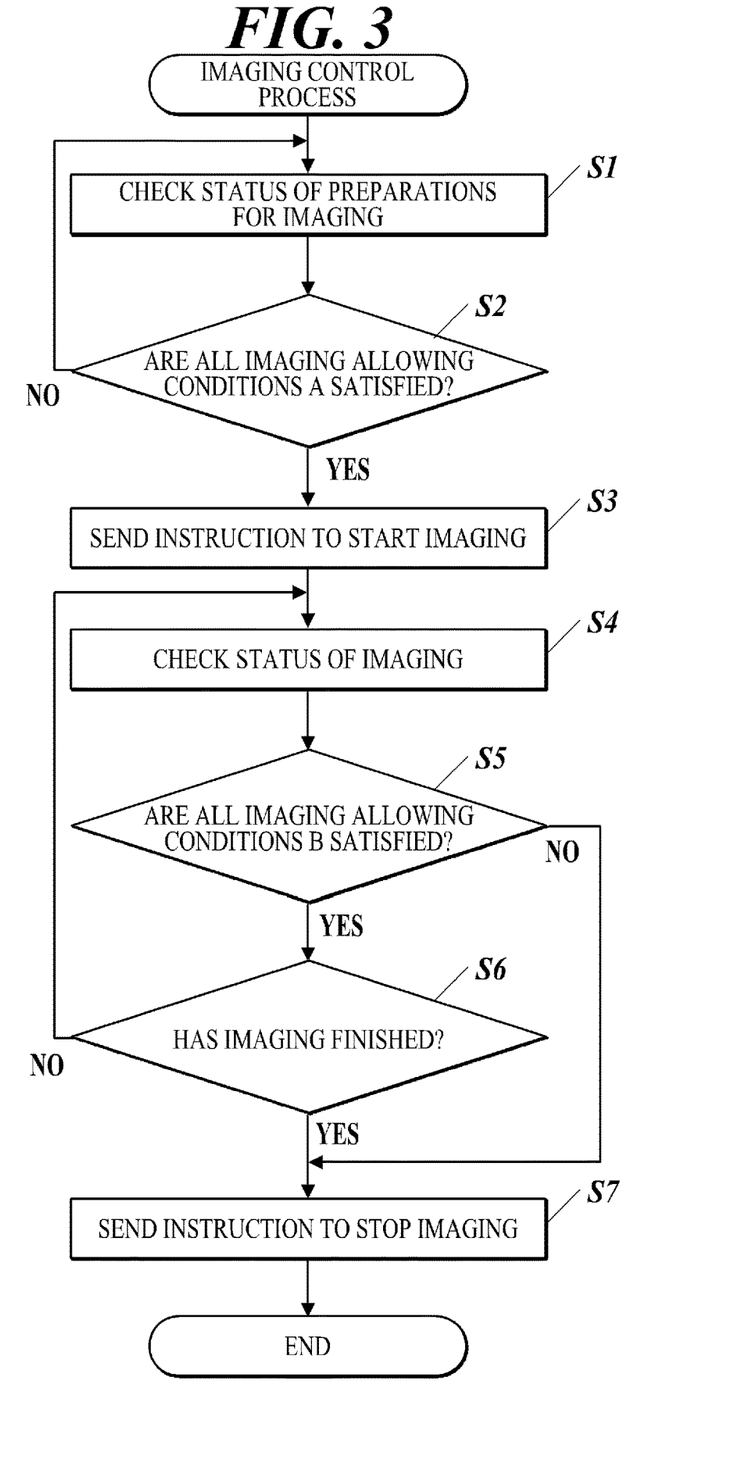
FIG. 3 is a flowchart of an imaging control process that is performed by the imaging control apparatus shown in FIG. 2.

The controller 31 performs an imaging control process shown in FIG. 3 by being triggered by a predetermined condition satisfied (e.g. when the console 3 is powered, when the console 3 (controller 31) receives an imaging order, when a predetermined operation for starting is performed on the operation unit 35, etc.).

In the imaging control process, the controller 31 first performs a process of checking the status of preparations for imaging (Step S1).

In this process, the controller 31 according to this embodiment checks the status of explanation of contents of imaging to an examinee (whether explanation has been given to an examinee), the result of a test of an audio guide (whether an audio guide works normally), the status of positioning of the examinee (whether the examinee is in the standing/decubitus position suitable for the imaging, whether the examinee is breathing normally, whether the examinee has practiced how to breath during the imaging, etc.), the status of preparation of each of the emitting apparatus 1 and the imaging apparatus 2, and the status of equipment of the examinee with an imaging aid(s).

Figure 4A:
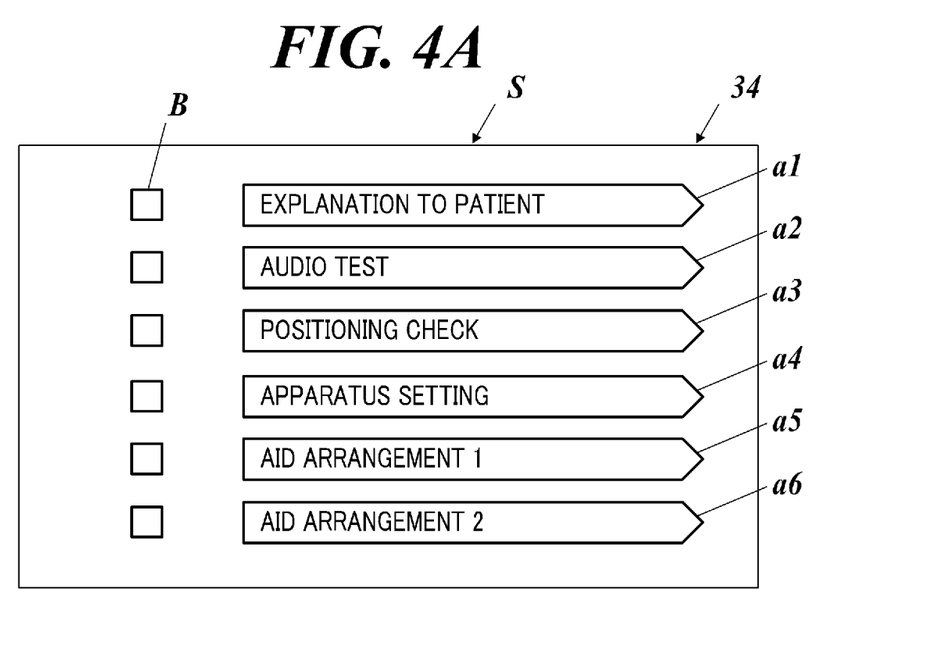
FIG. 4A shows an example of a check unit of the radiographic imaging system shown in FIG. 1.

In parallel with the process of Step S1, the controller 31 according to this embodiment performs a process of causing the display 34 to display, for example, a check screen S shown in FIG. 4A.

The controller 31 according to this embodiment causes the display 34 to display a list of preset imaging allowing conditions (items) a1 to a6, checkboxes B and/or the like on the check screen S.

The status of preparations for imaging may be checked manually or automatically. When the status of preparations for imaging is checked manually, the controller 31 receives user's check operations (predetermined operations).

When the user finishes one of the preparations for imaging and performs a check operation on the operation unit 35 (e.g. presses a key corresponding to an imaging allowing condition displayed on the check screen S, puts a cursor on an imaging allowing condition displayed thereon, touches the display section of an imaging allowing condition displayed thereon, etc.), the controller 31 assumes that a targeted imaging allowing condition has been satisfied (a targeted preparation for imaging has finished), and changes a display mode of an imaging allowing condition (item) corresponding to the check operation performed on the operation unit 35 among the displayed imaging allowing conditions (items).

More specifically, for example, the controller 31 causes the display 34 to display a checkmark in a checkbox displayed next to the imaging allowing condition, changes the display color of the imaging allowing condition, or moves the display section of the imaging allowing condition.

When two or more imaging allowing conditions are set, two or more check operations are performable on the operation unit 35 for the respective imaging allowing conditions.

Advancing the preparations for imaging in parallel with the checks using the check screen S can prevent the user from making a careless mistake in the preparations for imaging, reduce the time necessary for one time of imaging, and prevent the examinee from being restrained long uselessly.

Instead of causing the display 34 to display the check screen S, the controller 31 may cause, for example, a display of a portable terminal to display the check screen S.

Figure 4B:
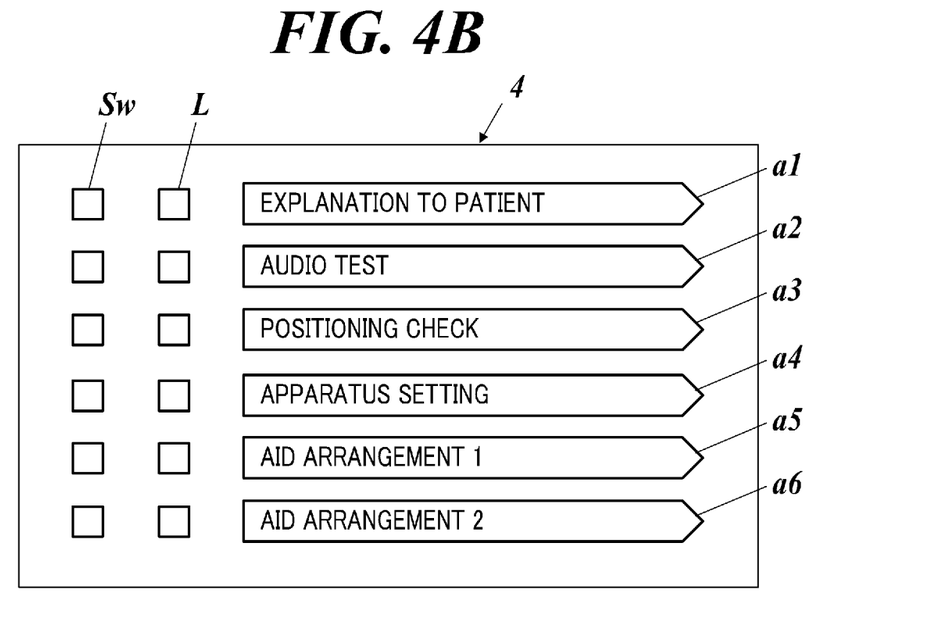
FIG. 4B shows another example of the check unit of the radiographic imaging system shown in FIG. 1.

Further, for example, a check apparatus 4 dedicated to receiving check operations may be used. As shown in FIG. 4B, the check apparatus 4 has a list of imaging allowing conditions (items) a1 to a6, switches Sw for the respective imaging allowing conditions operable by a user and lamps L for the respective imaging allowing conditions that light up when check operations are performed for their corresponding imaging allowing conditions.

The items for imaging allowing conditions displayed in the list are not limited to those (a1 to a6) shown in FIG. 4A and FIG. 4B, and hence may be items for other imaging allowing conditions. Examples of the other imaging allowing conditions (A) include: a condition that the ID of a photographer is correct (item: e.g. "Photographer ID"); a condition that the age of an examinee is correct (item: e.g. "Examinee's Age"); a condition that an examinee is (or is not) a pregnant woman (item: e.g. "Pregnant Woman"), an emergency patient (item: e.g. "Emergency Patient"), a handicapped person (e.g. deaf, blind, or able to have a specific posture only) (item: e.g. "Handicapped Person"), an injured patient (e.g. unable to stand without help) (item: e.g. "Injured Patient"), a patient equipped with an internal (built-in) aid, such as a pacemaker (item: e.g. "Internal-aid-equipped Patient"; and a condition that an examinee is a patient who has been subjected to the same examination multiple times (because such a patient does not need to practice how to breath or the like any more) (item: e.g. "Patient with Experience").

Further, regarding the number of items displayed in the list, because items to check in a medical checkup are often less than those in an examination proposed by a doctor, the number of items displayed in the list may be changed depending on whether imaging is imaging in a medical checkup or imaging in an examination proposed by a doctor. Further, the ID of each photographer is associated with information on a skill level (expert or not) of the photographer. Hence, the number of items displayed in the list may be changed depending on whether the photographer is an expert. For example, if the photographer is a rookie, the number of items to check may be eight, whereas if the photographer is an expert, the number of items to check may be reduced to five.

The operation device of the emitting apparatus 1 may have this function of receiving check operations.

In the above cases, the check apparatus 4 or the operation device of the emitting apparatus 1 acts as an operation unit (equivalent to the operation unit 35).

The check screen S may be displayed where the examinee can also see it.

This can show the examinee the remaining works for imaging intentionally. Thus, the check screen S allows the examinee to check whether the step of preparations for imaging is advancing properly and also provides the examinee with information for estimating the remaining work time. That is, the check screen S can be used as a tool for giving the examinee a sense of security.

On the other hand, when the status of preparations for imaging is checked automatically, the controller 31 first detects the status of each of the apparatuses electrically connected to the console 3, such as the emitting apparatus 1 and the imaging apparatus 2.

The controller 31 may detect the status of one of the apparatuses.

The controller 31 may detect user's voice (e.g. explanation being given to the examinee) through a microphone and the position or posture of the examinee through sensors or a camera.

If there is no problem in the detected status of each apparatus, the controller 31 assumes that a targeted imaging allowing condition has been satisfied (a targeted preparation for imaging has finished), and changes the display mode of an imaging allowing condition (item) corresponding to the statuses of the emitting apparatus 1 and the imaging apparatus 2 detected by itself among the displayed imaging allowing conditions (items).

More specifically, the controller 31 causes the display 34 to display a checkmark in a checkbox displayed next to the imaging allowing condition, changes the display color of the imaging allowing condition, or moves the display section of the imaging allowing condition.

In the process of Step S1, the controller 31 may use the manual checking and the automatic checking in combination.

After checking the status of preparations for imaging, the controller 31 according to this embodiment determines on the basis of the result of checking whether all of the set imaging allowing conditions A are satisfied (Step S2) as shown in FIG. 3.

Because the controller 31 has not yet instructed the emitting apparatus 1 to start operating, the controller 31 performs the process of Step S2 before the emitting apparatus 1 emits radiation (predetermined timing)

The controller 31 according to this embodiment determines whether check operations have been performed for all of the set imaging allowing conditions (items) a1 to a6 (whether checkmarks are displayed in all of the checkboxes).

If the controller 31 determines that all of the imaging allowing conditions A are satisfied (e.g. check operations have been performed on the operation unit 35 or the like for all of the set imaging allowing conditions, so that checkmarks are displayed in all of the checkboxes) (Step S2; YES), the controller 31 performs a process of allowing at least one of the emitting apparatus 1 and the imaging apparatus 2 to operate (Step S3). In other words, if the controller 31 determines that one or more of the set imaging allowing conditions is not satisfied (there is at least one checkbox without a checkmark), the controller 31 does not allow the emitting apparatus 1 and the imaging apparatus 2 to operate.

In this process, the controller 31 according to this embodiment sends, to the emitting apparatus 1, an emission allowing signal that allows emission of radiation (i.e. releases an interlock of the emitting apparatus 1), and sends, to the imaging apparatus 2, a control signal that is an instruction to shift to the standby state, for example.

In the case where the imaging apparatus 2 has a function of detecting irradiation and automatically starting generating a radiograph(s), the controller 31 may be configured to allow only the emitting apparatus 1 to operate.

The emitting apparatus 1 (hardware processor) may have a function of performing the process of Step S3.

On the other hand, if the controller 31 determines in Step S2 that at least one of the checkboxes for the imaging allowing conditions A is without a checkmark, namely determines that not all of the imaging allowing conditions A are satisfied (Step S2; NO), the controller 31 returns to Step S1.

Thus, the controller 31 according to this embodiment does not allow imaging to start unless all of the set imaging allowing conditions A are satisfied.

Although the controller 31 according to this embodiment determines in Step S2 whether all of the imaging allowing conditions A are satisfied, the controller 31 may determine whether at least one (e.g. an imaging allowing condition(s) A having a higher degree of importance) of the imaging allowing conditions A is satisfied.

The emitting apparatus 1 (hardware processor) may have a function of performing the process of Step S2.

When the controller 31 according to this embodiment determines that not all of the imaging allowing conditions A are satisfied (Step S2; NO), the controller 31 performs a predetermined notifying process.

Specifically, the controller 31 causes the display 34 to display a message indicating that an imaging allowing condition(s) is not satisfied or an instruction to satisfy the imaging allowing condition(s).

More specifically, the controller 31 causes the display 34 to display contents of an item(s) that has not been performed yet, or highlights an item(s) that has not been performed yet among the items a1 to a6 in the list of imaging allowing conditions displayed on the check screen S.

In the case where the emitting apparatus 1 includes a display (not shown), the display of the emitting apparatus 1 may display a message indicating that an imaging allowing condition(s) is not satisfied or an instruction to satisfy the imaging allowing condition(s).

In the case where the system 100 includes a portable terminal (wearable terminal included) (not shown), a display of the portable terminal may display a message indicating that an imaging allowing condition(s) is not satisfied or an instruction to satisfy the imaging allowing condition(s).

In addition to or instead of the display 34 displaying such a message (instruction), a speaker (not shown) may output sound, or a lamp (not shown) may light up, for example. In this case, a speaker or a lamp included in the emitting apparatus 1, the imaging apparatus 2 or an imaging table (not shown) may be used for the predetermined notifying process.

After causing the emitting apparatus 1 and the imaging apparatus 2 to operate (to start imaging), the controller 31 checks the status of imaging (Step S4).

In this process, the controller 31 according to this embodiment checks the position of the imaging target part of the examinee (whether the part is in the irradiation field), the dose of radiation, presence/absence of body motion of the examinee and the amount thereof, and presence/absence of a request to stop from the examinee.

The position of the imaging target part, the dose of radiation, and presence/absence of body motion of the examinee and the amount thereof may be checked by analyzing a radiograph(s) generated by the imaging apparatus 2 or by using various sensors, for example.

It is possible that an imaging period is divided into an early stage (immediately after start of imaging) and a middle stage according to, for example, the number of frames to be generated by imaging, and the position of the imaging target part and the dose of radiation are checked in the early stage, and the other items are checked in the middle stage or over the entire imaging period.

After checking the status of imaging, the controller 31 according to this embodiment determines on the basis of the result of checking whether all of the set imaging allowing conditions B are satisfied (Step S5).

Because the controller 31 has not yet instructed the emitting apparatus 1 to finish operating, the controller 31 performs the process of Step S5 while the emitting apparatus 1 is emitting radiation (predetermined timing).

If the controller 31 determines that all of the imaging allowing conditions B are satisfied (Step S5; YES), the controller 31 determines whether imaging has finished, namely whether imaging of the last frame has finished (Step S6).

If the controller 31 determines in Step S6 that imaging has not finished yet (Step S6; NO), the controller 31 returns to Step S4.

On the other hand, if the controller 31 determines in Step S6 that imaging has finished (Step S6; YES), the controller 31 instructs the emitting apparatus 1 and the imaging apparatus 2 to stop operating (Step S7) and ends the imaging control process.

If the controller 31 determines in Step S5 that one or more of the imaging allowing conditions B is not satisfied (Step S5; NO), the controller 31 instructs the emitting apparatus 1 and the imaging apparatus 2 to stop operating (Step S7) and ends the imaging control process.

Although the controller 31 according to this embodiment determines in Step S5 whether all of the imaging allowing conditions B are satisfied, the controller 31 may determine whether at least one of the imaging allowing conditions B is satisfied.

The emitting apparatus 1 (hardware processor) may have a function of performing the process of Step S5 (and Step S6) and a function of performing the process of Step S7.

In the imaging control process, after Step S3 (instructing the emitting apparatus 1 and/or the imaging apparatus 2 to start imaging), the controller 31 may end the imaging control process without performing the processes of Step S4 and the subsequent steps.

Alternatively, the controller 31 may perform the processes of Step S3 and the subsequent steps without performing the processes of Step S1 and Step S2.

That is, the timing at which the controller 31 determines whether imaging allowing conditions are satisfied may be only before the emitting apparatus 1 emits radiation or only while the emitting apparatus 1 is emitting radiation.

Further, if the controller 31 determines in Step S5 that not all of the imaging allowing conditions B are satisfied, and instructs the emitting apparatus 1 and the imaging apparatus 2 to stop operating (interrupts imaging) in Step S7, the controller 31 may obtain an operation-stopped log.

This makes it possible to analyze a trend of occurrence of improperness on the basis of the obtained operation-stopped log and take countermeasures against the improperness, and consequently reduce occurrence of improperness during imaging.

[3. Advantageous Effects]

When the system 100 including the console 3 (imaging control apparatus) according to the above embodiment is used for imaging, the user can confirm that imaging allowing conditions have been satisfied by operating the operation unit. Consequently, it is possible, in radiographic imaging, to prevent imaging from starting without proper preparations or continuing despite occurrence of improperness.

As a result, it is possible to reduce cases that require re-imaging, and consequently prevent examinees from being excessively restrained and uselessly exposed to radiation In radiographic imaging, which includes dynamic imaging, imaging allowing conditions to be satisfied may differ depending on the imaging environment. Further, before imaging starts or while imaging is being performed, two or more imaging allowing conditions may need to be satisfied.

The conventional technologies cannot deal with such difference in the imaging environment (difference in the number and/or contents of imaging allowing conditions for starting imaging or continuing imaging).

The console 3 according to the above embodiment, however, can select and set an imaging allowing condition from a plurality of candidates, and also can select and set a plurality of imaging allowing conditions therefrom as needed. Hence, the system 100 including this console 3 can prevent imaging from starting without proper preparations or continuing despite occurrence of improperness, regardless of the imaging environment.

In radiographic imaging (imaging of a still image or a dynamic image), imaging allowing conditions may include a condition that a preparation necessary to be performed by a person has been performed (e.g. the condition that explanation has been given to an examinee).

However, the conventional technology for preventing imaging from starting in a state in which preparations for imaging have not finished and the conventional technology for preventing imaging from continuing in a state in which improperness occurs can dealt with only situations (conditions) the satisfaction or dissatisfaction of which can be detected mechanically, such as a situation where captured data has been erased and a situation where body motion of an examinee has not been detected.

Hence, in imaging using either of the conventional technologies, preparations necessary to be performed by a person still could be forgotten.

Then, the radiographic imaging system of the present disclosure includes: the radiation emitter that emits radiation; the image generator that generates a radiograph(s) according to received radiation; the hardware processor that determines at a predetermined timing whether at least one imaging allowing condition is satisfied, and in response to determining that the at least one imaging allowing condition is satisfied, allows at least one of the radiation emitter and the image generator to operate; and the operation unit operable by a user, wherein based on whether a predetermined operation(s) has been performed on the operation unit, the hardware processor determines whether the at least one imaging allowing condition is satisfied. When the user confirms that he/she has performed a preparation and performs a predetermined operation on the operation unit (the check screen S of the console 3 or the check apparatus 4) (so that a checkmark is displayed), it is determined that an imaging allowing condition is satisfied. This can eliminate human error.

Although one or more embodiments of the present invention have been described and illustrated in detail, the disclosed embodiments are made for purposes of not limitation but illustration and example only. The scope of the present invention should be interpreted by terms of the appended claims

What is claimed is:

1. A radiographic imaging system comprising a plurality of components including:
 a radiation emitter that emits radiation;
 an image generator that generates a dynamic image composed of a plurality of frames according to received radiation; and
 a hardware processor that
  detects a status of a component of the plurality of components, the status corresponding to at least one imaging allowing condition,
  automatically determines at a predetermined timing whether the at least one imaging allowing condition is satisfied based on a result of the detection, and
  in response to determining that the at least one imaging allowing condition is satisfied, allows at least one of the radiation emitter and the image generator to operate,
 wherein the at least one imaging allowing condition includes at least one of a condition that positioning of an examinee has been performed and a condition that the examinee is equipped with an imaging aid.

2. The radiographic imaging system according to claim 1, wherein in response to determining that one or more of the at least one imaging allowing condition is not satisfied, the hardware processor does not allow the radiation emitter and the image generator to operate.

3. The radiographic imaging system according to claim 1, wherein the predetermined timing, at which the hardware processor determines whether the at least one imaging allowing condition is satisfied, includes at least one of (i) before the radiation emitter emits the radiation and (ii) while the radiation emitter is emitting the radiation.

4. The radiographic imaging system according to claim 1, further comprising a storage that stores a plurality of imaging-allowing-condition candidates, wherein
 the hardware processor sets, as the at least one imaging allowing condition, at least one imaging-allowing-condition candidate selected based on a user's choice from the plurality of imaging-allowing-condition candidates.

5. The radiographic imaging system according to claim 1, further comprising an operation unit operable by a user, wherein
 based on whether a predetermined operation has been performed on the operation unit, the hardware processor determines whether the at least one imaging allowing condition is satisfied.

6. The radiographic imaging system according to claim 5, wherein the at least one imaging allowing condition includes two or more imaging allowing conditions,
 wherein as the predetermined operation, two or more operations are performable on the operation unit for the respective imaging allowing conditions,
 wherein the hardware processor determines whether the operations have been performed on the operation unit for the respective imaging allowing conditions, and
 wherein in response to determining that all the operations have been performed on the operation unit, the hardware processor allows the at least one of the radiation emitter and the image generator to operate.

7. The radiographic imaging system according to claim 5, wherein the at least one imaging allowing condition is displayed in a form of a list, and
 wherein among the at least one imaging allowing condition displayed, the hardware processor changes a display mode of an imaging allowing condition corresponding to the predetermined operation performed on the operation unit.

8. The radiographic imaging system according to claim 1, wherein the hardware processor detects a status of the at least one of the radiation emitter and the image generator, and
 wherein based on the detected status of the at least one of the radiation emitter and the image generator, the hardware processor determines whether the at least one imaging allowing condition is satisfied.

9. The radiographic imaging system according to claim 8, wherein the at least one imaging allowing condition is displayed in a form of a list, and
 wherein among the displayed at least one imaging allowing condition, the hardware processor changes a display mode of an imaging allowing condition corresponding to the detected status.

10. The radiographic imaging system according to claim 3, wherein the at least one imaging allowing condition the satisfaction or dissatisfaction of which is determined before the radiation emitter emits the radiation includes at least one of: a condition that an explanation has been given to an examinee; a condition that an audio guide has been tested; the condition that positioning of the examinee has been performed; a condition that the radiation emitter and the image generator are ready; and the condition that the examinee is equipped with an imaging aid.

11. The radiographic imaging system according to claim 3, wherein the at least one imaging allowing condition the satisfaction or dissatisfaction of which is determined while the radiation emitter is emitting the radiation includes at least one of: a condition that an imaging target part of the examinee is in an irradiation field; a condition that a dose of the radiation is in a predetermined range; a condition that the examinee has not moved more than a predetermined amount; and a condition that no request to stop has been made by the examinee.

12. The radiographic imaging system according to claim 1, wherein in response to determining that one or more of the at least one imaging allowing condition is not satisfied, the hardware processor performs a predetermined notifying process.

13. An imaging control apparatus comprising a hardware processor that
 detects a status of a component of a radiographic imaging system corresponding to an imaging allowing condition,
 determines at a predetermined timing whether at least one imaging allowing condition is satisfied based on a result of the detection, and
 in response to determining that the at least one imaging allowing condition is satisfied, allows at least one of an radiation emitter that emits radiation and an image generator that generates a dynamic image composed of a plurality of frames according to received radiation to operate,
 wherein the imaging allowing condition is at least one of a condition that positioning of an examinee has been performed and a condition that the examinee is equipped with an imaging aid.

14. The imaging control apparatus according to claim 13, wherein in response to determining that one or more of the at least one imaging allowing condition is not satisfied, the hardware processor does not allow the radiation emitter and the image generator to operate.

15. The imaging control apparatus according to claim 13, wherein the predetermined timing, at which the hardware processor determines whether the at least one imaging allowing condition is satisfied, includes at least one of (i) before the radiation emitter emits the radiation and (ii) while the radiation emitter is emitting the radiation.

16. The imaging control apparatus according to claim 13, further comprising a storage that stores a plurality of imaging-allowing-condition candidates, wherein
the hardware processor sets, as the at least one imaging allowing condition, at least one imaging-allowing-condition candidate selected based on a user's choice from the plurality of imaging-allowing-condition candidates.

17. The imaging control apparatus according to claim 13, further comprising an operation unit operable by a user, wherein
based on whether a predetermined operation has been performed on the operation unit, the hardware processor determines whether the at least one imaging allowing condition is satisfied.

18. The imaging control apparatus according to claim 13, wherein the hardware processor detects a status of the at least one of the radiation emitter and the image generator, and
wherein based on the detected status of the at least one of the radiation emitter and the image generator, the hardware processor determines whether the at least one imaging allowing condition is satisfied.

19. The imaging control apparatus according to claim 13, wherein in response to determining that one or more of the at least one imaging allowing condition is not satisfied, the hardware processor performs a predetermined notifying process.

20. A radiographic imaging method comprising:
detecting a status of a component of a radiographic imaging system corresponding to an imaging allowing condition,
determining at a predetermined timing whether at least one imaging allowing condition is satisfied based on a result of the detection, and
in response to determining that the at least one imaging allowing condition is satisfied, allowing at least one of an radiation emitter that emits radiation and an image generator that generates a dynamic image composed of a plurality of frames according to received radiation to operate,
wherein the imaging allowing condition is at least one of a condition that positioning of an examinee has been performed and a condition that the examinee is equipped with an imaging aid.

21. A radiographic imaging system comprising:
a radiation emitter that emits radiation;
an image generator that generates a dynamic image composed of a plurality of frames according to received radiation; and
a hardware processor that
determines at a predetermined timing whether at least one imaging allowing condition is satisfied, and
in response to determining that the at least one imaging allowing condition is satisfied, allows at least one of the radiation emitter and the image generator to operate,
wherein the imaging allowing condition is a condition that an examinee has practiced how to breathe.

* * * * *